United States Patent
Archibald et al.

(10) Patent No.: US 7,033,542 B2
(45) Date of Patent: Apr. 25, 2006

(54) HIGH THROUGHPUT SCREENING WITH PARALLEL VIBRATIONAL SPECTROSCOPY

(76) Inventors: William B. Archibald, 1021 Grebe St., Foster City, CA (US) 94404; Alfred W. Archibald, 2323 Summit Dr., Hillsborough, CA (US) 94010

( * ) Notice: Subject to any disclaimer, the term of this patent is extended or adjusted under 35 U.S.C. 154(b) by 86 days.

(21) Appl. No.: 10/366,464

(22) Filed: Feb. 14, 2003

(65) Prior Publication Data
US 2003/0175160 A1 Sep. 18, 2003

Related U.S. Application Data

(60) Provisional application No. 60/356,111, filed on Feb. 14, 2002.

(51) Int. Cl.
*G01N 21/27* (2006.01)
*G01N 21/00* (2006.01)

(52) U.S. Cl. .................. 422/82.09; 422/50; 422/58; 422/82.05; 422/82.11; 250/339.01

(58) Field of Classification Search ............... 436/164, 436/165, 172; 422/55, 58; 250/339.01, 250/341.8
See application file for complete search history.

(56) References Cited

U.S. PATENT DOCUMENTS

| | | |
|---|---|---|
| 4,130,107 A | 12/1978 | Rabl et al. |
| 4,240,692 A | 12/1980 | Winston |
| 4,382,656 A | 5/1983 | Gilby |
| 4,891,120 A | 1/1990 | Sethi et al. |
| 5,194,133 A | 3/1993 | Clark et al. |
| 5,254,858 A | 10/1993 | Wolfman et al. |
| 5,361,160 A | 11/1994 | Normandin et al. |
| 5,416,325 A | 5/1995 | Buontempo et al. |
| 5,585,069 A | 12/1996 | Zanzucchi et al. |
| 5,658,413 A | 8/1997 | Kaltenbach et al. |
| 5,777,736 A | 7/1998 | Horton |
| 5,858,804 A | 1/1999 | Zanzucchi et al. |
| 5,872,010 A | 2/1999 | Karger et al. |
| 5,980,704 A | 11/1999 | Cherukuri et al. |
| 6,033,628 A | 3/2000 | Kaltenbach et al. |
| 6,093,330 A | 7/2000 | Chong et al. |
| 6,158,712 A | 12/2000 | Craig |
| 6,176,962 B1 | 1/2001 | Soane et al. |
| 6,180,536 B1 | 1/2001 | Chong et al. |

(Continued)

FOREIGN PATENT DOCUMENTS

WO   WO 9815813 A1 *   4/1998

(Continued)

OTHER PUBLICATIONS

Hansen et al. "Spectrometer Cells for Single and Multiple Internal Reflection Studies in Ultraviolet, Visible, Near Infrared, and Infrared Spectral Regions", Anal. Chem., 1964, vol. 36, No. 4. pp. 783-787.*

(Continued)

*Primary Examiner*—Yelena G. Gakh
(74) *Attorney, Agent, or Firm*—Heller Ehrman LLP

(57) ABSTRACT

Rapid spectrum assay of multiple samples with infrared light is made possible by devices and methods that increase total light throughput. Multiple wavelength scan with Fourier analysis is combined with large numbers of sample wells located within infrared light compatible solid materials. In particular, very large scale measurement devices and systems for their use are fabricated from lithography and other techniques used for semiconductor processing.

32 Claims, 12 Drawing Sheets

U.S. PATENT DOCUMENTS

| | | |
|---|---|---|
| 6,210,986 B1 | 4/2001 | Arnold et al. |
| 6,245,227 B1 | 6/2001 | Moon et al. |
| 6,306,272 B1 | 10/2001 | Soane et al. |
| 6,331,439 B1 | 12/2001 | Cherukuri et al. |
| 6,570,158 B1 * | 5/2003 | Feygin ....................... 250/332 |

FOREIGN PATENT DOCUMENTS

| | | |
|---|---|---|
| WO | WO 99/05509 A1 | 2/1999 |

OTHER PUBLICATIONS

Lewis et al. "Fourier Transform Spectroscopic Imaging Usingan Infrared Focal-Plane Array Detector", Anal. Chem., 1995, vol. 67, pp. 3377-3381.*

Snively et al. "Fourier-Transform Infrared Imaging Using a Rapid-Scan Spectrometer", Optics Letters, 1999, col. 245, No. 24, pp. 1841-1843.*

Snively et al. "Chemically Sensitive High Throuput Parallel Analysis of Solid Phase Supported Library Members", J. Comb. Chem., 2000 v. 2, pp. 243-245.*

Snively et al. "Parallel Analysis of the Reaction Products from Combinatorial Catalyst Libraries", Angew. Chem. Int. Ed., 2001, v. 40, No. 16, pp. 3028-3030.*

Shilov et al. "Mid-IR evanescent-wave sensors for tiny biological samples", Proceedings of SPIE—The International Society for Optical Engineering (2000), 3918, pp. 202-207.*

* cited by examiner

HIGH THROUGHPUT SCREENING WITH PARALLEL VIBRATIONAL SPECTROSCOPY

This application claims priority to U.S. Provisional Application Ser. No. 60/356,111, Feb. 14, 2002.

FIELD OF THE INVENTION

The invention relates generally to methods and apparatus for rapid spectrum assay of multiple samples using total internal reflection and related techniques, and in particular to methods and sample holders for optically studying large numbers of chemistries simultaneously.

BACKGROUND OF THE INVENTION

Virtually every area of the biomedical sciences needs to determine the presence, structure, and function of particular analytes that participate in chemical and biological interactions. The needs range from the basic scientific research lab, where biochemical pathways are being mapped and correlated to disease processes, to clinical diagnostics, where patients are routinely monitored for levels of clinically relevant analytes. Other areas include pharmaceutical research, military applications, veterinary, food, and environmental applications. In all of these cases, the presence, quantity, and structure activity relationships of a specific analyte or group of analytes needs to be determined.

Numerous methodologies have been developed to meet this need. The methods include enzyme-linked immunosorbent assays (ELISA), radio-immunoassays (RIA), numerous fluorescence assays, mass spectrometry, colorimetric assays, gel electrophoresis, as well as a host of more specialized assays. Most of the assay techniques require specialized preparations such as chemically attaching a label or purifying and amplifying a sample to be tested. Generally, an interaction between two or more molecules is monitored via a detectable signal relating to the interaction. Typically a label conjugated to either a ligand or anti-ligand of interest generates the signal. Physical or chemical effects produce detectable signals. The signals may include radioactivity, fluorescence, chemiluminescence, phosphorescence, and enzymatic activity. Spectrophotometric, radiometric, or optical tracking methods can be used to detect many labels.

Unfortunately, in many cases it is difficult or even impossible to label one or all of the molecules needed for a particular assay. The presence of a label may interrupt molecular interaction or otherwise make the molecular recognition between two molecules not function for many reasons including steric effects. In addition, none of these labeling approaches can determine the exact nature of the interaction. Active site binding to a receptor, for example, is indistinguishable from non-active site binding, and thus no functional information is obtained from the present detection methodologies. A method to detect interactions that eliminates the need for the label and that yields functional information would greatly improve upon the above mentioned approaches.

Detection technology is commercially very important. The biomedical industry relies on tests for a variety of water-based or fluid-based physiological systems to evaluate protein-protein interactions, drug-protein interactions, small molecule binding, enzymatic reactions, and to evaluate other compounds of interest. Ideally, the technology should not require highly specific probes, such as specific antibodies. The assay should operate by measuring the native properties of molecules and would not require additional label(s) or tracer(s) to detect a binding event. In many applications, the assay should be miniaturizable and handle samples in parallel, so that complex biochemical pathways can be mapped out, or extremely small and numerous quantities of compounds can be used in drug screening protocols. For many applications, the assay should monitor in real time, a complex series of reactions, such that accurate kinetics and structure-activity relationships can be obtained almost immediately.

Vibrational spectroscopy overcomes limitations in this field and is a well established, non-destructive, analytical tool that can reveal much information about molecular interactions. Infrared spectroscopy involves the absorption of electromagnetic radiation generally between 0.770–1000 microns (12,900–10 cm$^{-1}$), which represent energies on the order of those found in the vibrational transitions of molecular species. Variations in the positions, widths, and strengths of these modes with composition and structure allow identification of molecular species. One advantage of infrared spectroscopy is that virtually any sample, in virtually any state, can be studied without the use of a separate label. Liquids, solutions, pastes, powders, films, fibers, gases, and surfaces can be examined by a judicious choice of sampling techniques. Biological systems such as proteins, peptides, lipids, bio-membranes, carbohydrates, pharmaceuticals, foods, and both plant and animal tissues have been characterized with infrared spectroscopy as reviewed by B. Stuart in *Modem Infrared Spectroscopy* (Wiley and Sons) Chichester (1996) and in *Biological applications of Infrared Spectroscopy* (Wiley and Sons) Chichester 1997.

The availability of high-resolution infrared spectrometers has led to time resolved investigations of chemical and biological interactions, which include cell cycle investigations (e.g. H. Y. Holman, M. C. Martin, E. A. Blakely, K. Bjornstad, W. R. McKinney, *Biolpolmers (Biospectroscopy)* 2000, 57, 329–335), protein-protein interactions (e.g. R. Barbucci, A. Magnani, C. Roncolini, S. Silvestri, *Biopolymers* 1991, 31, 827–834), polymerization studies (e.g. P. K. Aldridge, J. J. Kelly, J. B. Callis, D. H. Burns, *Anal. Chem.* 1993, 65, 3581–3585), and solid-phase organic reactions (e.g. B. Yan, J. B. Fell, G. Kumaravel, *J. Org. Chem.* 1996, 61, 7467–7472). These investigations traditionally have been restricted to one-at-a-time measurements because of single detectors used for conventional infrared spectrometers. Autosamplers have been introduced, which move either the optical path over the samples or a number of samples through the optical path sequentially using a computer controlled system. See for example, http://www.optics.bruker.com/pages/products/BIO/hts-xt.htm; http://www.piketech.com/catalog/pdfs/autotrns.pdf. However, data collection mostly remains serial, making kinetic investigations cumbersome, if not impossible, for a large number of reactions.

Serial one-sample investigations also have been addressed by detector arrays such as a focal plane array which uses infrared spectral imaging for remote sensing, as described by R. Beer *Remote sensing by Fourier transform spectrometry* (Chemical Analysis v. 120) 1992, Wiley and Sons, New York. Spectral imaging also has been coupled to use of an infrared microscope (See for example U.S. Pat. No. 5,377,003 and references therein and B. Foster, *American Laboratory* Feb. 21–29, 1997, and P. J. Treado, M. D. Morris, *Applied Spectroscopy Reviews* 1994, 29(1), 1–38) for imaging studies of plant and animal tissue, polymer dissolution, and polymer liquid crystals. These single sample procedures purport to collect spatially correlated spectral information (i.e. a spectral image). More recently, infrared spectra have been made from multiple samples in parallel and is particularly advantageous for high throughput screening of the large numbers of chemical products in combinatorial investigations. For example, published patent application WO 98/15813 describes the use of parallel detection infrared spectroscopy for monitoring catalytic reactions and other applications of high resolution imagery for "single samples" (see http://www.spectraldimensions.com). This patent application describes measurements primarily in the transmission mode but unfortunately, lacks information needed to make a realistic system. For example, the discussion and figures of sample holders for the transmission measurements do not explain how to transfer samples into a sample array. The assumption presented that a robot would fill sample arrays and then a human would have to "cap" the arrays with an infrared transparent "top" is impractical for an automated high-throughput screening environment. Thus, this described system at best appears limited to the high-resolution imagery on "single-samples."

Unfortunately, these systems suffer sensitivity and/or speed limitations. One reason is that as sample number increases the actual size of a single decreases. The number of photons that can interact with the sample in a short time to generate a meaningful signal decreases dramatically and generally limits both sensitivity and speed. A solution to this problem would open up new areas of discovery and would be particularly important in the burgeoning field of combinatorial chemistry, which require rapid assay of huge numbers of very tiny samples.

SUMMARY

Embodiments of the invention provide a higher throughput analysis of multiple samples and allow real time assay of molecules in their natural environment. Multiple samples are analyzed using an instrument for performing-parallel vibrational spectroscopy, comprising a source of broadband infrared radiation for probing molecular interactions with a modulator of broadband infrared radiation, a multiple well sample holder comprising a substrate with an array of wells, a light directing optical structure having an optical interface with each sample well, wherein the optical structure directs modulated broadband infrared radiation to each said sample well, allowing internal reflection and subsequent exit of the altered light, an infrared imaging radiation detector for simultaneously detecting the altered light, and a computer for analyzing data from the infrared imaging radiation detector.

Another embodiment provides a sample holder suitable for simultaneous assay of molecular interactions in multiple wet samples via parallel vibrational spectroscopy, comprising a semiconductor substrate, an array of at least 96 wells for accepting fluid, wherein at least one prismatic feature optically couples to each well and an internal reflection element extending into each well that is optically coupled the a prismatic feature and provides internal reflections within the well. Yet another embodiment provides a method of manufacturing a sample holder for simultaneous assay of molecular interactions in multiple wet samples via parallel vibrational spectroscopy, the holder comprising a semiconductor substrate, an array of wells in the substrate, and at least one internal reflection element extending into each well, the method comprising repeated anisotropic wet etching of the semiconductor substrate to form a two dimensional array of at least 96 wells wherein each prismatic feature has a mean width of between 5 and 100 microns and has a mean height of between 10 and 10000 microns.

Yet another embodiment is a sample holder for the simultaneous assay of molecular interactions in multiple wet samples via parallel vibrational spectroscopy, comprising a substrate for holding an array of at least 96 sample wells, and a prismatic structure for each sample well, wherein the prismatic structure comprises a material that is transparent to broadband infrared light of wavelengths between 5 and 10 microns, is at least twice as tall as it is wide and allows the light to enter the optically dense material with an incidence angle that exceeds the critical angle for total internal reflection.

Yet a further embodiment is a tool for detecting effects of chemical compounds on cellular activities or for detecting desirable genetic manipulations in vitro, comprising a source of broadband infrared radiation having wavelengths longer than 5 nanometers, a temperature controlled wet cell sample holder having at least 16 wells that hold and maintain metabolizing cells at a constant temperature, wherein each well has at least one surface in contact with the cells that is transparent to the infrared radiation, one or more prismatic structures for directing the broadband infrared radiation into the infrared radiation transparent surfaces with an incidence angle that exceeds the critical angle for total internal reflection that penetrates a layer of cells in contact with the surface, and an infrared imaging detector that collects reflected light.

Yet another embodiment is a high throughput method for monitoring a reaction involving a set of biomolecules in solution, comprising immobilizing or synthesizing the set of biomolecules on an array surface with different species of biomolecules at discrete immobilizing locations of the array surface, wherein the array surface is transparent to infrared radiation longer than 5 microns wavelength and each immobilizing location is in optical contact with a prismatic structure that directs infrared light with longer than 5 micron wavelength into the array surface with an incidence angle that exceeds the critical angle for total internal reflection that penetrates at least one micron of the solution, irradiating the array surface with broadband infrared radiation of wavelengths longer than 5 nanometers, collecting reflected broadband light spectra from each immobilized location, and calculating multiple absorbance values for the immobilizing locations using Fourier transform.

Yet another embodiment combines multiple infrared sources with parabolic reflectors to generate high intensity light and uses one or more prismatic structures for directing light onto multiple samples.

Yet another embodiment combines visible light and infrared light for simultaneous wide spectral analyses of molecular interactions. Such interactions include short wavelength interactions associated with fluorescence, chemiluminescence and absorbance of chemical moieties of higher energy pi electrons, such as those found in aromatic residues of proteins.

Yet another embodiment enhances signal development by biochemically focusing optical targets to within one half wave period of the probing light, through one or more binding reactions that precede the optical signal development.

Yet another embodiment enhances the performance of drug discovery techniques for chemicals that interact with membrane protein systems, wherein attenuated total internal reflection of biomolecules at cell surfaces is achieved using infrared light with wavelengths that exceed 2 microns and wet samples having intact cells or microsomes immobilized at a probed surface to allow focus on events associated with the membrane proteins.

DETAILED DESCRIPTION

Figure 1:
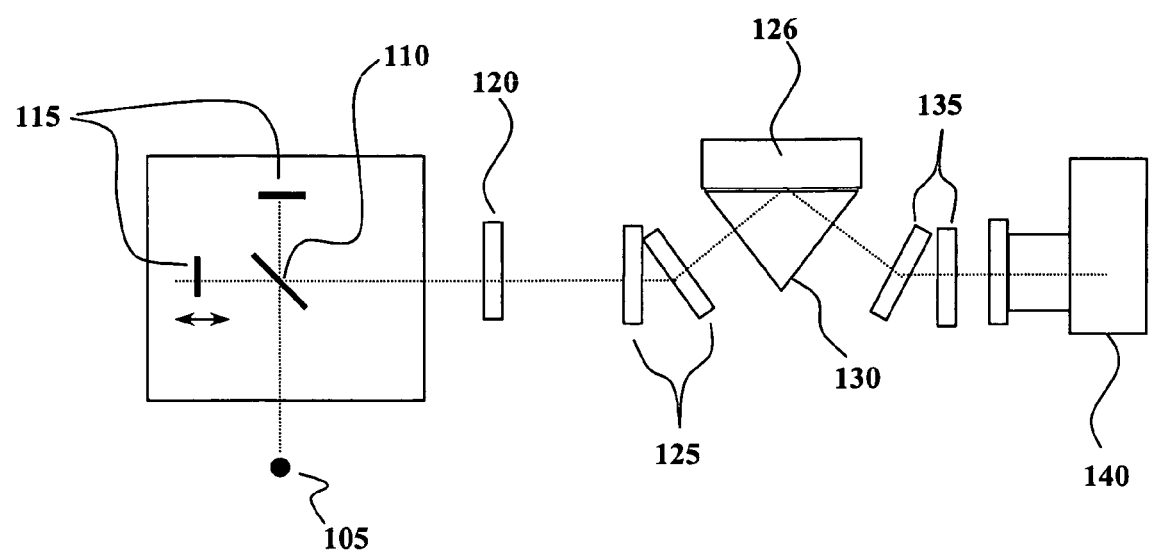
FIG. 1 shows a schematic outline of optics used for reflectance measurements of attenuated total reflection according to an embodiment.
Figure 2:
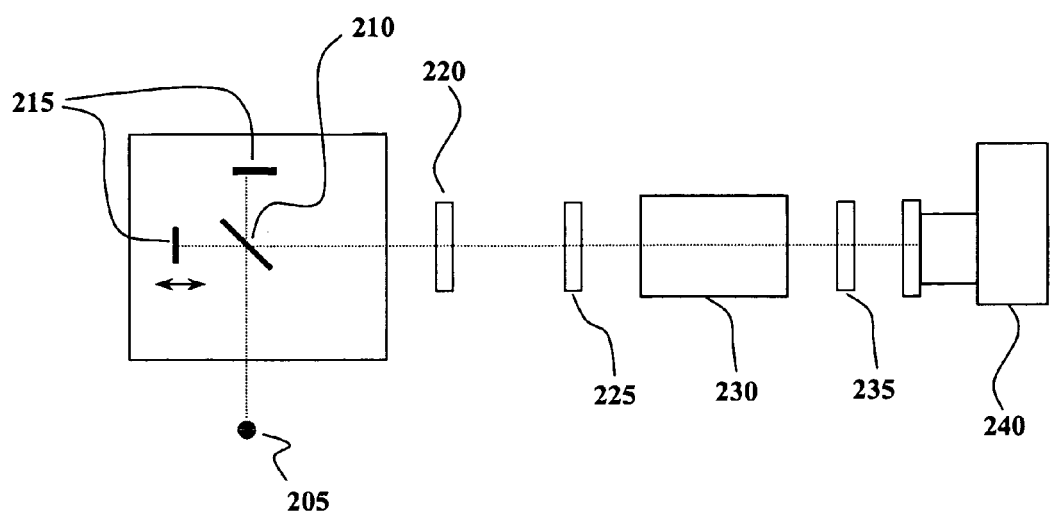
FIG. 2 is a schematic diagram of an imaging spectrometer for transmission measurements according to an embodiment of the invention.

The inventors studied the problem of multiple sample spectroscopy with a total system viewpoint and realized that the quantity of light processed per sample is a major limitation to the assay of many small samples simultaneously. That is, the spectroscopic analysis of a large number of samples in parallel requires a much higher flow of total light to obtain parallel information for each sample simultaneously. This system obstacle was addressed by: i) increasing the amount of starting light with parabolic optics and multiple light sources; ii) adopting a high bandwidth system that uses wide spectrum light and Fourier analysis, allowing much higher light fluxes and consequent information flow; iii) discovery of prismatic structures and alternative sample formats that greatly increase light throughput while permitting large sample numbers; iv) discovery of miniature sample holder designs that can be mass produced by semiconductor processing techniques; and v) discovery of biochemical and cellular focusing techniques that further optimize signal energy use for improved signal to noise. Each of these discoveries contributes to improved performance, singly and in combination, and facilitates the use of higher sample number spectroscopic assays, as further detailed below.

Wide Bandwidth Systems for Multiple Sample Assays

Embodiments of the invention utilize light spectra of multiple wavelengths to measure absorption and/or transmission spectra from arrays of multiple samples simultaneously. In contrast to many previous techniques, the high bandwidth systems of embodiments of the present invention use entire spectral regions, combined with Fourier analysis, for much greater total light usage and real time detection of individual wavelengths without requiring narrow light filtering. Most other spectroscopic systems discard the vast majority of light from a light source via bandpass filtering or by use of a diffraction grating and selection of a wavelength. The high bandwidth and Fourier analysis are particularly desirable in combination with prismatic structures and small sized but high sample number assay targets.

Fourier transform methods used in embodiments of the invention are known and hae been used for spectroscopy and for total internal reflectance as exemplified in U.S. Pat. No. 5,416,325 issued to Buontempo et al., May 16, 1995. The contents of this patent, and particularly the described methods for maximizing the ratio of signal to noise for low light intensity signals specifically are incorporated by reference in their entireties. The contents of U.S. Pat. No. 5,777,736 issued to Horton on Jul. 7, 1998; U.S. Pat. No. 5,254,858 issued to Wolfman et al. on Oct. 19, 1993; U.S. Pat. No. 4,382,656 issued to Gilby on May 10, 1983; U.S. Pat. No. 4,240,692 issued to Winston on Dec. 23, 1980; U.S. Pat. No. 4,130,107 issued to Rabl et al. on Dec. 19, 1978; and U.S. Pat. No. 5,361,160 issued to Normandin et al. on Nov. 1, 1994 also provide details for use of Fourier transform spectroscopic methods are particularly incorporated by reference, and represent art known to the skilled artisan.

Light from a light source is modulated and an interferometer for this purpose preferably is used within a light passageway having focusing and/or beam steering optics to manage the light beam. The managed beam contacts (by reflection or transmission) each sample simultaneously and then is directed toward the detector, which preferably is a two dimensional detector. The detector collects data simultaneously from the samples and transfers the data to a computer for storage and processing.

The interferometer may be placed on the source side to interrupt the probing light before contact with sample or it may be on the detector side to interrupt the light between the sample and the detector. In either embodiment the interferometer modulates the light prior to detection by the detector. For embodiments that utilize infrared light, as much of the beam path as possible should be in a controlled environment to limit error due to water absorption. It is highly desirable to control the amount of water vapor and carbon dioxide in the environment surrounding the sample to achieve a stable baseline. Drift in the temperature, humidity, or chemical content of the medium through which the light beam passes during a measurement may change the spectra in an uncontrolled manner. Such change complicates the mathematical subtraction of the background, making it difficult and/or unreliable. In a preferred embodiment dry nitrogen gas is added to spaces where the infrared beam passes on the way to and from a sample.

Representative Instrumentation An example of a reflectance mode apparatus according to embodiments of the invention is provided in FIG. 1, which shows a light source, detector and some parts between the source and detector, Light from light source 105 passes through beam splitter 110 and is reflected by interferometer mirrors 115 into spectral filter 120. Light from spectral filter 120 is focused via focusing and beam steering optics 125 into the bottom of sample holder 130 having optical interface 126 in optical contact with each sample well. The light then interacts with each sample in one or more passes and is then reflected out of sample holder 130 and is focused by optics 135 infrared camera 140. An embodiment of this system as shown in FIG. 1 comprises five components: 1) source of infrared radiation, 2) a device to modulate the radiation, 3) a sample holder, 4) an infrared detector, and 5) a computer to collect, process, and present the spectral data.

An example of a transmission mode apparatus in accordance with an embodiment of the invention is shown in FIG.

2. Here, radiation from source 205 passes through beam splitter 210 and is reflected by interferometer mirrors 215 into spectral filter 220. Light from spectral filter 220 is focused via focusing optics 225 into the bottom of sample holder 230, where each element of a sample array within holder 230 is illuminated simultaneously. Radiation passes through the samples and then is focused by optics 235 and enters infrared camera 240.

Transmission Mode Sample Holders Transmission measurements are carried out by passing light from a source through a sample and to a detector and generally require different sample holders than that used for reflectance measurements. Solution based infrared transmission measurements generally require a short path length transmission cell or a flow-through cell. In both configurations the optical path length through the sample is restricted to short distances such as about 5–10 microns in length for aqueous solutions. A sample may be sandwiched between two infrared transparent windows separated by a thin gasket (Teflon) designed to confine the sample and fix the path length. A similar sample holder exists where the sample flows through a pipe with an infrared transparent sidewall to let light in and out. Neither configuration allows simultaneous acquisition of infrared absorption spectra from multiple samples. The problems of multiple transmission measurements in parallel can thus be stated as requiring: i) a separation of all samples in an infrared beam; ii) control of the required short path lengths; and iii) reduction of solvent evaporation.

Figure 3:
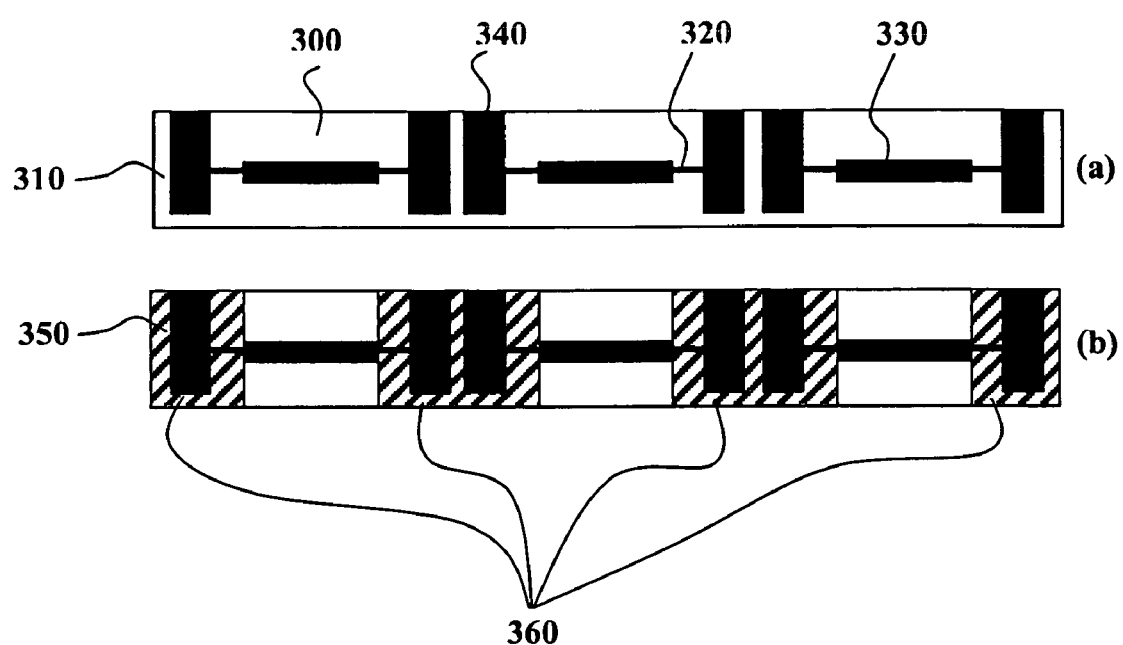
FIG. 3 shows representative sample holders for transmission measurements according to embodiments of the invention.

These problems were successfully addressed by the discovery of a parallel sample holder design as exemplified in FIG. 3. This sample holder has several features that alleviate these problems. First, the holder contains infrared transparent regions to let the beam pass through the sample. These infrared transparent sampling regions may be created by constructing the entire holder from an infrared transparent medium, or by integrating a series of infrared transparent windows into a non-transmitting matrix. Second, the sample holders contain specific sample injection ports, as seen in FIG. 3. Each sample location may have several sample injection ports to allow combination of reactants, solvents, etc. Finally, the sample injection ports are connected to the infrared sampling region by microchannels, which allow the sample to move from the port to the sampling region by capillary action. The capillary fed, short path-length sampling regions can be modified as suited to limit the beam path through the sample and isolation as needed to reduce solvent evaporation.

More specifically, FIG. 3a shows sample holder 300 having three sampling units constructed with infrared transparent material. As seen for the left hand most unit, sample injection/removal port 310 is used to add or remove a sample or a sample stream that flows through capillary micro channel 320 into sampling region 330 and then out sample injection/removal port 340. Sample holder 350 shown in FIG. 3b further includes non-transparent matrix regions 360.

The infrared transparent regions of these sample holders can be made of one or more infrared transparent materials such as an alkali halide salt (KBr or NaCl), $CaF_2$, $BaF_2$, ZnSe, Ge, Si, thin polyethylene, or specialized infrared materials such as AMTIR and KRS-5. The use of materials such as Si and Ge allow the entire sample array to be microfabricated using lithography and standard semiconductor processing techniques. The non-transmitting matrix can be made of a low cost material such as a plastic, glass, wax, polymers, elastomers, and so on.

Internal Reflectance Mode Sample Holders and Components Further embodiments were discovered that provide superior attenuated total internal reflectance for multiple samples through use of new prismatic structures that direct light for optimum effect, as detailed below. To place these several discoveries in context, a brief summary of how attenuated total internal reflectance spectroscopy works is provided along with a description of how certain discoveries relevant to this procedure are used. Based on this information, a skilled artisan may further optimize the presented embodiments for particular sample arrangements.

Many embodiments of the invention use attenuated total internal reflectance spectroscopy for samples that are very strong infrared absorbers, such as water. In these embodiments a beam of energy entering an optical cell undergoes total internal reflection at the interface between the sample and the optical cell when the angle at which the incident light impacts the sample/sample holder interface is greater than the critical angle. The critical angle is material dependent and based on Snell's Law. The angle is defined by the indices of refraction for the sample and the optical cell. This angle is particularly important to the dimensions and placement of prismatic structures according to embodiments of the invention. This is because a surface skimming (evanescent) wave is created when light impinges at the fluid sample surface at or above the critical angle. This surface-skimming wave reacts with the sample in close proximity to the interface between the sample and the optical cell, and then exits the cell.

Prismatic structures as discovered and described below are dimensioned for and positioned to control probing light to enter a sample/sample container boundary so as to enter the boundary at an angle equal to or (more preferably) greater than the critical angle. In an embodiment a prismatic structure controls a probing light spectrum beam to enter a sample/container boundary within 2degrees of a critical angle determined for light of wavelength in the middle of the beam spectrum. In another embodiment the light beam is controlled to enter at 0–2, 0–5, 0–15, 0–30, 0–45, 5–10, 5–15, 5–30, 15–45 or even 0 45 degrees greater than the critical angle. In another embodiment a prismatic transparent structure is dimensioned and positioned to direct a probing light spectrum beam to enter a solid medium at an angle that is more perpendicular to the solid medium, in order to minimize reflective losses.

The penetration of a probing light spectrum beam into a sample is short, typically on the order of the wavelength of the incident light (Equation 1). This eliminates the need to control and measure the path length or volume of the sample during the measurement. This feature allows more convenient and inexpensive use of multiple sample arrays that may be placed in optic communication with the probing beam and a detector with less need for precision. Heavily absorbing samples with thicknesses greater than 1 mm can be measured with this configuration.

$$\text{Penetration Depth} = \frac{\lambda/n_1}{D_p = 2\pi[\sin\theta - (n_1/n_2)^2]0.5}$$

Such optical cells may be fabricated into individual crystals and preferably, for infrared measurements, are made of infrared transparent materials such as, for example silicon, germanium, zinc selenide, AMTIR, and KRS-5.

The use of attenuated total internal reflection has been exploited by others and a variety of components useful for building instruments are available. However, generally, such instruments have been strictly limited to the use of single samples. For high throughput analysis of many biological samples, prismatic structures and other features as detailed herein are combined, as discussed next.

Prismatic Designs for High Sample Throughput The inventors discovered several prismatic designs, devices and methods of their use that greatly improve the capability of total internal reflectance assay of large numbers of samples in parallel. Generally, the prismatic properties of carefully dimensioned optic devices are chosen to control the probing light (light that contacts the sample interface for reflectance measurements) to enter a sample interface at a suitable angle. Embodiments of the invention provide devices wherein probing light simultaneously enters multiple sample/well interfaces at different locations. Moreover, the devices maintain approximately the same (i.e. within 10 degrees, preferably within 5 degrees, more preferably within 2 degrees and preferably within 1 degree of a standard deviation) incident light angle into each sample. Preferably, the incident light angle is greater than the critical angle throughout the entire array.

Three types of advantageous sample holders for attenuated total internal reflectance measurements were discovered. A first type maintains substantially equivalent optic treatment of multiple samples through optical contact of a large optic device that acts as a large common prismatic device for all samples. The large optic device directs light into and out of each sample simultaneously. In a preferred embodiment the outer surface of the large optic device is dimensioned so as to direct light simultaneously into sample wells at an incidence angle that equals or exceeds the critical angle, as seen in FIG. 4.

Figure 4:
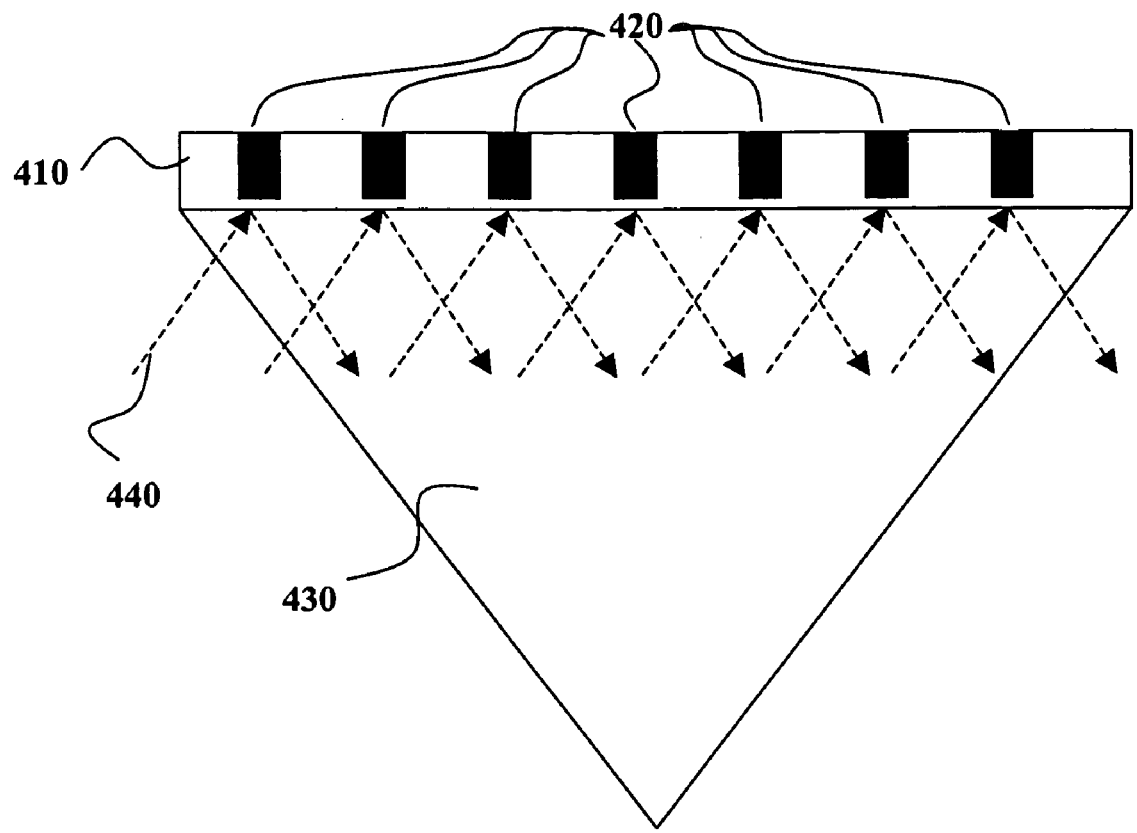
FIG. 4 shows a prismatic device for attenuated total reflection according to an embodiment.

FIG. 4 shows the use of a fabricated array of attenuated total reflectance sample holders 410. Array 410 consists of sample wells 420 capable of holding fluid, particularly aqueous liquid, or solid samples. Optical interface prismatic device 430 contacts the bottom of array 410 and is capable of directing infrared radiation beam 440 from outside to the interface with the sample under appropriate conditions for internal reflection. In the arrangement shown in FIG. 4, infrared radiation beam 440 is incident on the surface of transparent prismatic device 430 and enters holder 410. The infrared radiation interacts with sample wells 420 and the other sample wells and then reflects away from sample holder 410 as depicted in the broken lines.

In a desirable embodiment large prismatic device 430 is a fixed part of the optics of an instrument and array 410 is separable, allowing sample processing and manipulation away from the machine. In an embodiment array 410 comprises infrared transparent material and is re-used. In another embodiment that uses visible light, array 410 comprises visible light transparent material such as an inexpensive plastic and is disposable. A preferred sample array device is a microtiter plate, particularly having 96 wells or a multiple of 96 wells such as 384, 1536 or 3072 wells. A preferred size of an array is for a length of approximately 108 millimeters and a width of approximately 75 millimeters. In an embodiment the sample array is processed by robotics used for regular microtiter plates having at least 96 wells.

A variety of shapes and dimensions may be used according to the discovered structures and features described here. For example, FIG. 5 shows a sample array 510 that is in contact with a large prismatic hemisphere 520 having a curved surface that bends probing light beams (see light beam 530) to enter the array such that the light beam meets or exceeds the critical angle at the surface between the sample and the transparent material of 510 in contact with the sample.

Figure 5:
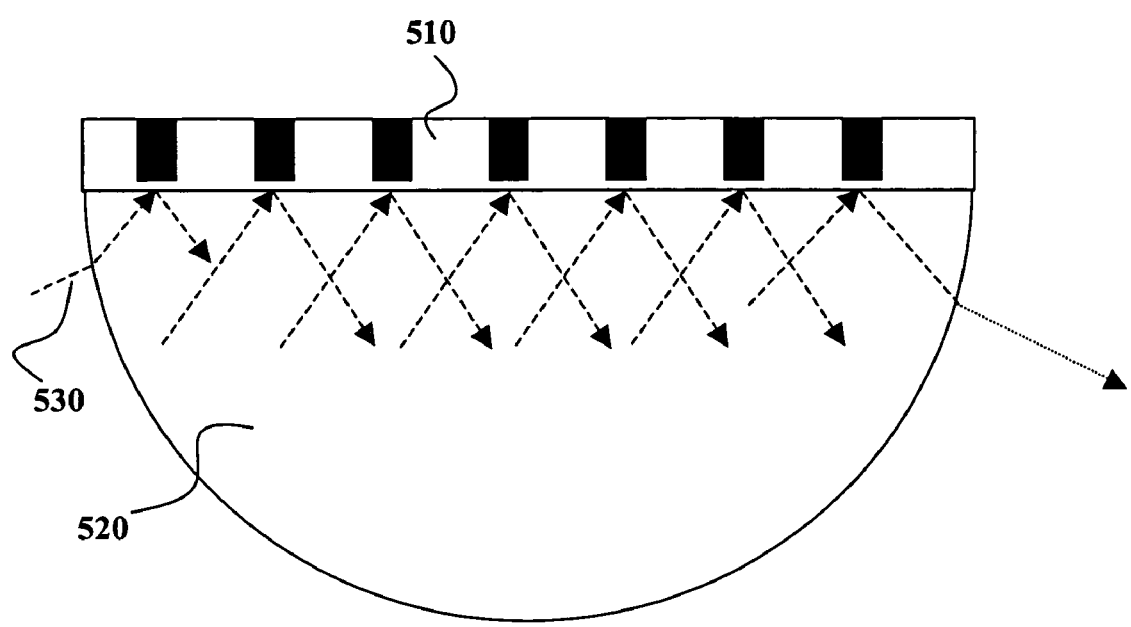
FIG. 5 shows a hemispheric surface for attenuated total reflection according to an embodiment.

As exemplified in FIGS. 4 and 5, a transparent prismatic material shown as 420 and 520 in these figures, respectively may be the same material as that use for the sample holder. A prism or hemisphere shape as shown in these figures is particularly advantageous but other shapes may be used. In the embodiments of FIGS. 4 and 5 the transparent prismatic material contacts the flat bottom of the sample holder and directs light beams that typically are parallel and enter different sample surfaces in a reproducible manner.

The reflection/transmission efficiency is strongly dependent on the angle of incidence between the light and the optical medium. A normal incidence results in the maximum transmission and minimum reflection. Therefore adding an optical structure such as that shown in FIGS. 4 and 5 allows light to enter the optically dense material at near normal incidence for reduced reflective losses and increased light throughput to the sample. The transmission efficiency can be further improved by adding a broadband anti-reflection coating to the optical structure.

The prismatic or hemispheric optic (structures 430 and 520 in the figures) can remain in the instrument allowing the sample holder to be removed and replaced. The interface between the flat bottom of the sample holder and the prismatic or hemispheric optic is not perfect, meaning there may be a slight air gap due to non-uniformity. This gap would represent a location for further reflective losses. To overcome this, an index matching fluid is used to fill the gap. Most advantageously the refractive index of the fluid has a numeric value that is between the refractive indexes of the two material surfaces and more preferably is midway (within 20% of the mean value), between the two solid phase refractive indexes.

Figure 6:
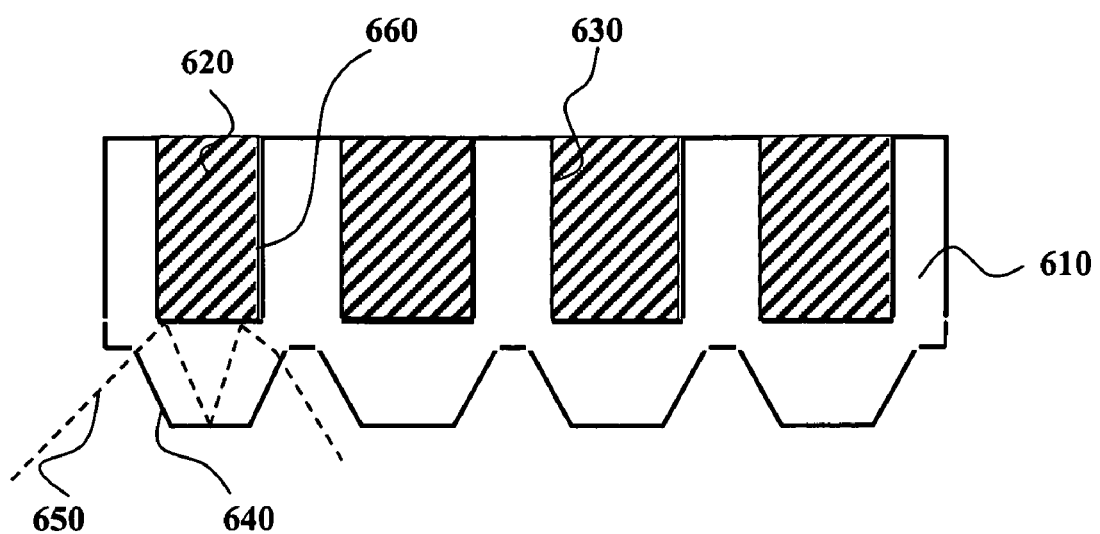
FIG. 6 shows an attenuated total reflection sampling assay according to an embodiment.

A second type of geometrical arrangement uses separate prismatic portions adjacent to each sample surface to direct light beams to interact with each sample in multiple locations before reflecting away from the sample holder. A prismatic sample array according to this second type is shown schematically in FIG. 6. Array 610 has wells 620 and walls 630. Walls 630 advantageously are opaque. Lower optical portion 640 of the left most sample allows light beam 650 to enter and undergo two reflections off lower sample surface 660 before exiting.

Typically the lower surface of a sample well establishes an attenuated total internal reflection with the sample and an adjacent optical portion (which may be continuous with the surface in contact with the sample or may be separate) is prismatic. In this case the lower surface ideally is a prism with a high aspect ratio, i.e. long length and short thickness. Advantageously the aspect ratio exceeds 1.5, 2, 3, 4, 5, 7, 8, or even 10. The prism allows the light to enter at near normal incidence for the reasons discussed above. Light becomes trapped between the upper and lower faces of the prism, similar to a fiber optic.

Figure 7:
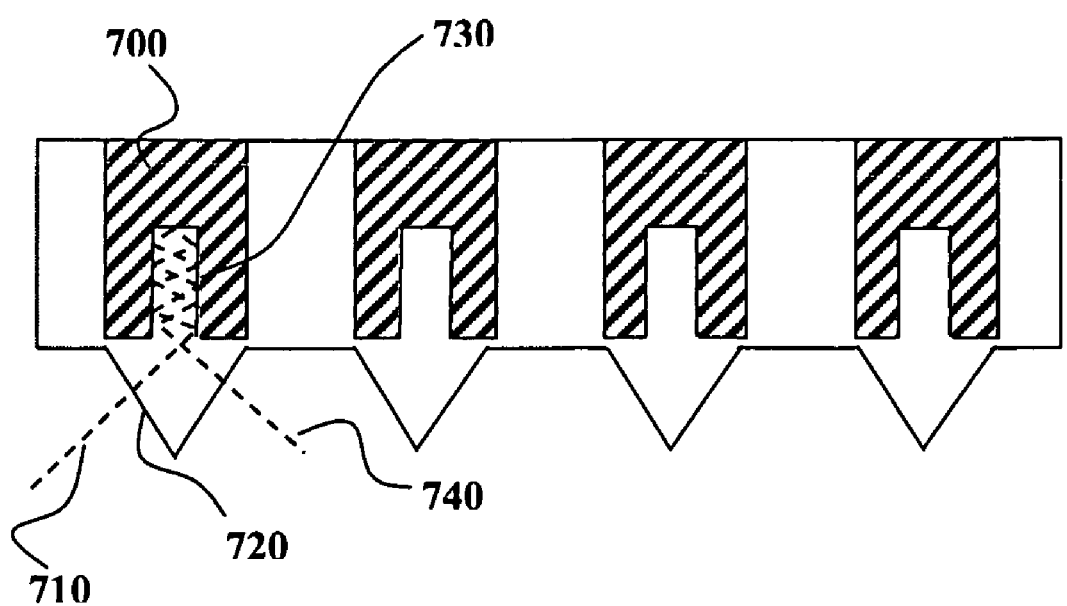
FIG. 7 shows a multiple internal reflection sampling assay according to an embodiment.

In the third type of geometrical arrangement a multiple internal reflection element protrudes into the sample well from an optical surface, and a prismatic optical surface is created at the optical surface. A representative array of multiple internal reflection elements is shown in FIG. 7. As seen in the left hand sample well 700 of FIG. 7, light beam 710 enters prismatic optical surface 720 on the lower optical surface and propagates up into multiple internal reflection element 730 where the radiation interacts with the sample at multiple locations before exiting as beam 740 from the prismatic surface on the lower optical surface.

Combinations of the three types of geometrical arrangements may be made and various dimensions will be appreciated by a skilled artisan Further Advantageous Features Spectral Filtering of Source Radiation A majority of contemplated applications require accumulating spectral information in the wavelength range between 5–16.5 microns (1 micron=$10^{-6}$ meters), or between 2000–600 $cm^{-1}$. Infrared sources emit radiation over a large wavelength range from the visible to the far infrared and embodiments of the invention use the various wavelengths. Infrared wavelengths outside a desired spectral window may adversely affect the measurement through sample heating. Uncontrolled heating in turn causes background (baseline signal) drift and decreases signal to noise ratio of measurements. Therefore, a spectral filter preferably is included to limit the infrared radiation from a source to a bandwidth of interest, and blocks other radiation generated from the source but which is not necessary for a measurement.

Such blocking is particularly valuable when light intensity is increased for small area samples (i.e. high power density applications). An infrared filter can be fabricated by deposition of a thin film(s) of specialized material(s) (metals and semiconductors) onto a infrared transparent substrate. The thin film layer(s) alters the transmission and reflection coefficients of the optical interface such as to limit the bandwidth of radiation allowed to pass through the filter. A general discussion can be found in many optical texts, at http://www.ocli.com/pdf files/products/geninfoinfraredfilters.pdf or in O. S. Heavens *Optical Properties of Thin Solid Films* 1991, Dover Press, New York.

Polarization Filters for Enhanced Performance Advantageous embodiments of the invention exploit the polarization properties of light to obtain additional information from the total internal reflection spectrum using a polarizing filter. In an embodiment a linearly polarized filter is placed in the beam path in front of the detector and thereby limits the infrared radiation entering the detector to a certain preferred polarization. Typically, the polarization is adjusted to allow either radiation polarized in the plane of reflection or perpendicular to the plane of reflection in order to enhance the signal of oriented thin film samples relative to the background. A photoelastic modulator optionally may be used to rapidly modify the polarization between left and right circularly polarized states, generally between 10 Hz and 10 MHz, preferably between 100 Hz and 1 MHz and more preferably between 1 KHz and 100 KHz frequencies. The detector measures the differential absorption of left vs. right circularly polarized infrared radiation. This differential polarization provides for the detection of stereochemical information, such as chirality. In an embodiment differential polarization allows the differentiation between enantiomers.

Modulation Modulation, combined with Fourier transform analysis is particularly powerful for improving signal and analysis time. Light from the source preferably is modulated with an interferometer. A preferred interferometer is a Michelson interferometer. Numerous other interferometer designs exist and are suitable. In principle any interferometer that creates an optical path difference will work in one or more embodiments.

Camera Speed and Spectral Resolution Many laboratory based mid-infrared imaging spectrometers utilize a Michelson interferometer to modulate infrared radiation before the radiation interacts with a sample. The Michelson interferometer often is used in commercial FT-IR spectrometers as the "light source" in their systems. The Michelson interferometer uses a moving mirror system to generate an optical path difference between two components of a split light source. The spectral resolution of a two-beam interferometer is based on the overall optical path difference in the interferometer and number of optical path differences at which the detector is read (number of mirror positions measured). The data from each of the optical path differences is converted to an absorption spectrum with the aide of a mathematical (e.g. Fourier) transform algorithm and a computer.

Two beam systems are capable of very wide bandwidths (25,000–13 $cm^{-1}$) and very high-resolution (~0.005 $cm^{-1}$) operation, and are particularly described as they are useful in embodiments of the invention. The need to move one or both mirrors complicates time sensitive analysis when the kinetics of the event being measured is on the same time scale as the mirror speed. In other words, the data are averaged over the time needed to sweep one length of the mirror path; speed and resolution are inversely related. Certain two-beam interferometers utilize a step-scan configuration, where the interferometer steps to a fixed optical path difference and scans a small amount (small mirror movement) around that path length.

The influence on imaging systems is even more profound due to the increased time needed to get the data from the array. The array speed generally scales with the size, the smaller arrays being faster, and single pixel detectors (found in FT-IR spectrometers) generally operate at MHz frequencies. A typical 64×64 pixel Hg—Cd—Te array has a maximum frame rate of 420 Hz, with specialized arrays allowing operation at ~1 kHz. Since an image must be taken for each optical path difference (mirror position), and the spectral resolution is dependent on the number of different mirror positions measured, higher resolution translates into longer times in the imaging sense as well.

Complicating the speed issue further, many chemical and biological reactions require numerous spectra that must be averaged for noise reduction prior to data processing. A typical protein experiment, for example, may require the combination of 100 or more spectra data for mathematical processing via one or more algorithms such as smoothing, derivatizing, curve-fitting, etc.). Embodiments of the invention provide rapid multiple spectra from each sample in an array which increases system performance and provides good sample throughput speeds Correction with an internal standard One of the largest contributors to noise when taking infrared measurements in aqueous solutions is drift in the background (baseline). This problem may be addressed by generating a background (baseline) measurement and then using that measurement to reference subsequent spectra. In many cases the stored baseline spectrum is subtracted from subsequent spectra. Typically the baseline will change due to changes in temperature or changes in the atmospheric conditions, such as changes to humidity, carbon dioxide content, etc. These changes manifest themselves as an incomplete subtraction or overcompensation of background effects. The drift problem is acute for measurements of dilute concentrations of molecules, where the baseline noise may overcome the desired signal from molecules in solution.

One method to alleviate the problem is to take a new baseline before every experiment or every time the background has changed. In long reactions the background may change often, requiring many new baseline measurements. Two methods are particularly desirable to rectify this increased noise problem.

One method of correction is to use photolabile groups to trigger chemical reactions and time the background measurements according to the triggering time. For example, a new baseline can be determined before every triggering event. Adding up the spectra acquired after every triggering event produces a spectrum more free of baseline changes.

Another method is to place one or more reference samples in one or more sample wells within the sample array; and use spectra obtained from the well(s) as a baseline for other samples in the array. For example, one well in a 96 well plate is filled with solution similar to all of the other wells, but containing no test molecule(s). Spectra collected from this well are used as baseline (reference) spectra. Spectra collected from the other 95 samples in the plate are referenced to the baseline spectra from the reference well. This method utilizes the power of parallel data acquisition to utilize one or more wells within the sample array as a reference for background changes. This correction procedure is particularly valuable for acquisition of multiple spectra over long reaction times such as minutes or even hours.

Binning for increased speed or sensitivity The slow speed of the infrared focal plane arrays is the primary limiting factor in data acquisition speed for this type of instrument. The parallel nature of spectral imaging slashes spectral averaging speed and compensates for the slower speed of the focal plane array. Generally, radiation from each sample in the field of view of the infrared detector strikes more than one pixel on the detector. Combining the intensity data from all such pixels for a given sample allows averaging of measurements from multiple single detectors, in a similar manner as described above for spectral averaging. For example, a typical data set from averaging 100 spectra can be obtained in 6 scans by binning the 16 pixels.

Binning is particularly effective for arrays of samples where the size of the sample array is smaller than the size of the focal plane array. A typical 384 sample array (16×24 samples) using a 64×64 element focal plane array would place approximately 5×2=10 pixels on each sample spot. Binning the 10 pixels reduces the required scans ten fold. A conventional FT-IR spectrometer may require 76 seconds to acquire 100 spectra at 4 cm$^{-1}$ resolution (mirror velocity at 1.58 cm/s). Replacing the detector with a focal plane array and binning the same 10 pixels would reduce this acquisition time to 7.6 seconds.

Generally, true imaging systems that work with true images are not able to exploit binning in this manner. Unlike the parallel array systems described herein, those systems need every pixel in an array to increase spatial resolution. Thus, the binning method described here runs counter to the needs in that related art. That is, improved acquisition speed for spectral averaging is specific to parallel data acquisition, and cannot be used where high spatial resolution is required. Preferred embodiments incorporate binning when gathering data and are at least ten fold faster than a non-binning machine. Where the sample array has more elements than the focal plane array, binning can still be employed if tiling is used, that is, through stitching together of multiple images.

Detectors A parallel infrared spectrometer for these purposes should have a detector sensitive to mid-infrared radiation in the 5 to 17 micron wavelength range. These detectors include such materials as Hg—Cd—Te, DTGS, thermopiles, quantum well infrared photodetectors (QWIP's), as well as many types of cooled and uncooled bolometers. In an imaging or parallel spectrometer, these detectors are found in either linear (1×128, 1×256, etc.) or rectangular arrays (64×64, 128×128, 4×256, etc.). The detector and read-out electronics form the components of an infrared camera. The camera converts the incoming radiation into a spectral image using mathematical transform algorithms on a standard personal computer.

Sample Holders and Solvents for Infrared A majority of chemical and biological reactions take place in aqueous or organic solvents that absorb mid-infrared radiation well. For example, strong absorption in the mid-infrared spectral region generally limits the optical path-length to 5–10 microns in aqueous solutions. Conventional one-at-a-time spectrometers typically use three approaches to obtain spectra in these environments. They include, short path length or flow-through cells, total internal reflectance, and solvent evaporation. Each approach is constrained by the need for infrared transparent sample holder(s), or at least regions in the holder that are transparent. Many embodiments described herein address this problem by (in comparison with earlier art) shrinking the sample size and assaying large numbers of samples simultaneously.

Infrared Light Sources and Focusing Embodiments of the invention provide diagnostic signals obtained by interaction of light with chemical bonding electrons found in molecules of interest. The diagnostic signals form from electric impulses that correspond to detected light signals. A good signal to noise (random electrical background signals) ratio thus is important to obtain rapid measurements because as the measurement time decreases the amount of light processed (and the electrical signal obtained from the light) becomes smaller. Infrared light is used in many embodiments wherein desired spectral processes involve fundamental vibrational resonances of molecules in the mid-infrared region of the light spectrum, which generally is defined as 4000–400 cm$^{-1}$ (2.5–25 microns).[1] A majority of biological compounds are limited to 1800–600 cm$^{-1}$ (5.5–16.7 microns).

To generate probing light in the infrared region, a blackbody emission source typically is used such as a "glowbar" (a hot material such as SiC), a sample or scene's intrinsic heat emission, or from solar infrared radiation. Preferred sources include a single glowbar (silicon carbide rod), Nernst glower (cylinder of rare-earth oxides) or an incandescent wire. A source typically may have power outputs of ~50–100W and a beam diameter of ~4 cm, or a beam power density of ~4W/cm$^2$. This power density can be increased with focusing optics for smaller samples, and reduced when an aperture is placed between the source and the sample. This power density is acceptable for traditional infrared experiments that involve a single sample in the beam path, or small area samples where the beam can be focused to a specific spot. In larger area sampling environments that exist when hundreds of small samples are to be measured simultaneously, broadening the beam to increase the effective area decreases the power density at each location in the sample. Therefore in order maintain an advantageous power density for an increased area of larger samples the infrared source power desirably is increased.

In one embodiment spectra are collected simultaneously from a "standard" micro titer plate format commonly used in the biological and chemical industry. These plates may hold an array of 96, 384, 768, 1536, 3072, 4608, 6144 or other number of sample wells. The relevant area of a titer-plate format sample holder is approximately 80 cm$^2$ and a source intensity of ~350W is necessary to produce the same 4 W/cm$^2$ at each sample location. This power optionally is increased to accommodate any apertures or optical losses in the beam path. A larger glowbar or Nernst source advantageously may be used for increased source intensity whereby a greater surface area on the source causes more emission.

Figure 8:
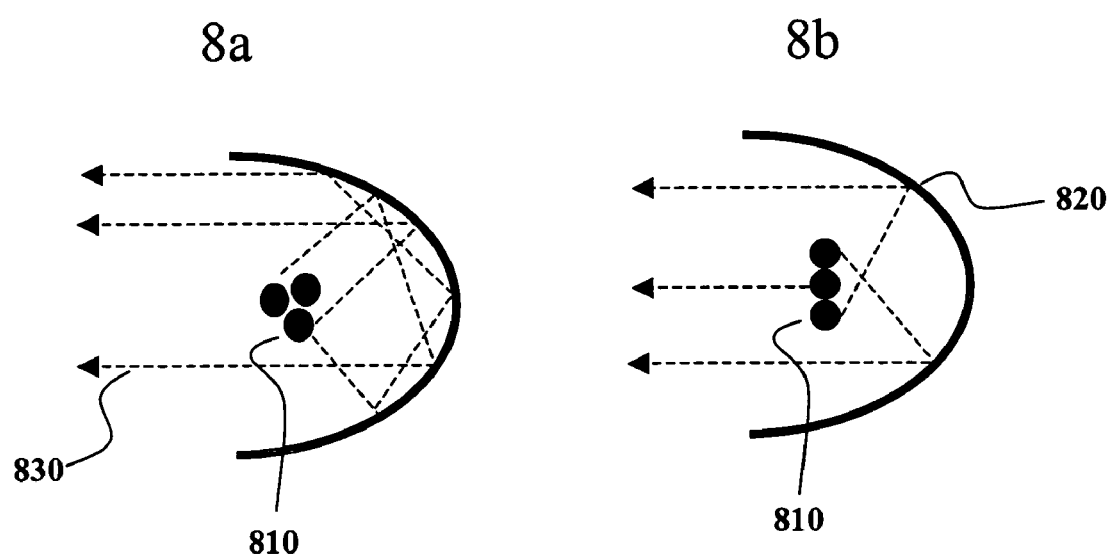
FIGS. 8a and 8b show the combination of multiple infrared sources with a mirror to increase the amount of parallel probing light according to an embodiment.

Alternatively multiple lower-intensity sources may be used in tandem. In the latter embodiment parabolic mirrors may be used to collect the light from several light sources and collimate it in the direction of the sample. Several embodiments of the latter are shown in FIG. 8. Three lower intensity sources 810 shown in FIGS. 8a and 8b may be positioned in a cluster or side by side, respectively, while allowing parabolic reflector 820 to direct the emitted light in a parallel fashion as shown by rays 830 in these Figures.

Biochemical and Cellular Focusing for Enhanced System Performance The attenuated total reflection methods described herein rely on the proximity of a surface skimming wave (evanescent field) from a probing light to a sample. Biochemical focusing and cellular focusing techniques were discovered that exploit the functional separation of the sample volume into a probed portion (available to the surface wave) and a non-probed portion (essentially too far away to measurably affect the wave). In both focusing techniques greater signal to noise is achieved for improved measurements by physically concentrating the target to a sub-portion of the sample volume where the surface skimming wave is.

Figure 9:
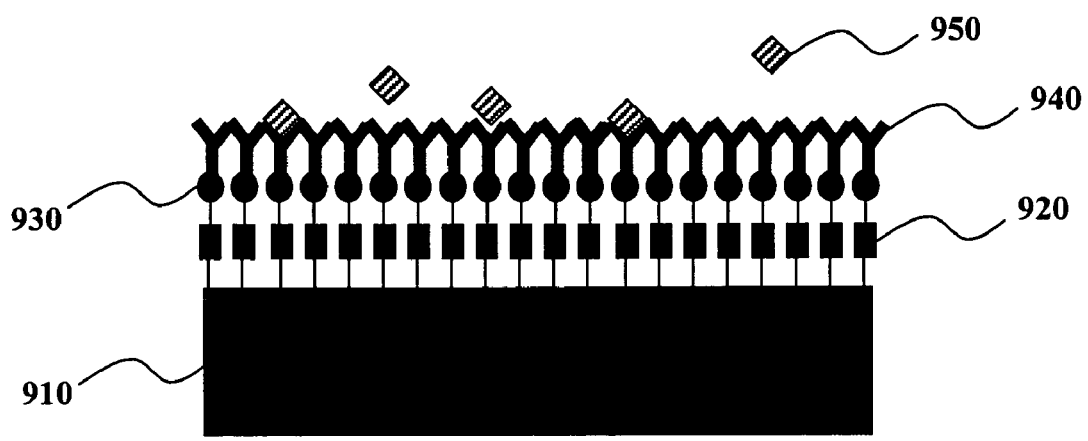
FIG. 9 shows a biospecific capture layer for parallel attenuated total reflectance according to an embodiment.

In biochemical focusing, molecule(s) are drawn out of solution and concentrate into a smaller volume that is exposed to a surface wave. The concentration step may be carried out by for example, a biochemical interaction layer. A representative embodiment is illustrated in FIG. 9. FIG. 9 shows optical surface 910 upon which surface coupling ligands 920 are immobilized. Surface coupling ligands 920 are in turn attached to spacer ligands 930, and thence to capture ligands 940. Analyte 950, which typically is present throughout the liquid media binds to capture ligand 940. The binding of analyte 950 to the capture layer effectively brings more of the analyte within reach of the surface wave, and thus increases the effect of the analyte on the signal.

Each element in the sample array shown in FIG. 9 can have a similar or a different interaction layer tailored to a desired biochemical interaction. Such surface binding layers have been used in many biosensor designs, and are very common in diagnostic applications. Binding layers typically involve a ligand to bind the layer to the surface, various spacer or coupling layers, and a capture ligand or protein, such as an antibody. Different ligands may be chosen for coupling to the surface, depending on the type of surface. Ligands for coupling to silicon generally will differ from ligands that couple to polyethylene for example. U.S. Pat. No. 5,851,840 issued to Sluka et al. and also U.S. Pat. No. 5,240,602 issued to Hammen for example describe ligands generally and also ways to bind molecules to silicon surfaces. The use of capture ligands is well known, as for example described by U.S. Pat. No. 6,264,825 issued to Blackburn, et al., U.S. Pat. No. 5,658,732 issued to Ebersole et al., U.S. Pat. No. 5,498,551 issued to de Jaeger et al. and many others.

In cellular focusing, molecular interactions that occur at the surface of or within a cell preferentially are probed using a probing light wavelength chosen to match or exceed the size of a cell, which is to lie within the surface wave region of the sample. In this embodiment, cells adhere to the sample surface where the surface skimming wave is made. Preferably the mean wavelength of the probing light that generates the surface skimming wave is at least 5 microns, more preferably at least 7.5 microns, and in some embodiments more than 10 microns and even more than 15 microns Preferably a cell is chosen having a thickness, (when lying flat on the sample surface) that is no more than twice the mean wavelength of the probing light and more preferably no more than the mean wavelength of the probing light. Preferential detection of molecular structures within cells, and at the cell surfaces are possible because the surface wave is chosen to be long enough to extend this far from the solid transparent medium but not long enough to cover most of the culture medium.

In another embodiment two types of probing light are used to discriminate between molecular events that occur close to the sample surface and those that occur further away. One light has a longer wavelength than the other and generates a more penetrating surface wave. For example, probing visible light of 600 nanometer wavelength may be used to obtain data for molecules and cell membrane surfaces that are attached to the surface. At the same time or at different times, probing light of 6000 nanometers may be used to obtain information for molecules and cell membrane surfaces that may be typically ten times further away from the optic surface.

Manufacture by Semiconductor Processing Techniques In an embodiment of the invention small arrays for simultaneous assay of many samples are prepared from semiconductor substrates. Such total internal reflectance arrays can be fabricated with standard lithographic processing found in the semiconductor industry. For example, one might use anisotropic wet etching of silicon or germanium and a photoresist to create prismatic features on a silicon substrate.

Suitable manufacturing techniques are described by, for example, U.S. Pat. No. 4,891,120 issued to Sethi et al., and other more recent U.S. Pat. Nos. 6,331,439; 6,306,272; 6,245,227; 6,210,986; 6,180,536; 6,176,962; 6,158,712; 6,093,330; 6,033,628; 5,980,704; 5,872,010; 5,858,804; 5,585,069; and 5,194,133. Laser ablation techniques also may be used to make these devices as described in U.S. Pat. No. 5,658,413 issued to Kaltenbach et al. on Aug. 19, 1997. A good general summary may be found in *Silicon Micromachining* (Cambridge Studies in Semiconductor Physics and Microelectronic Engineering, 7), M. Elwenspoek, H. V. Hansen, Cambridge University Press (Cambridge), 1999.

Figure 10:
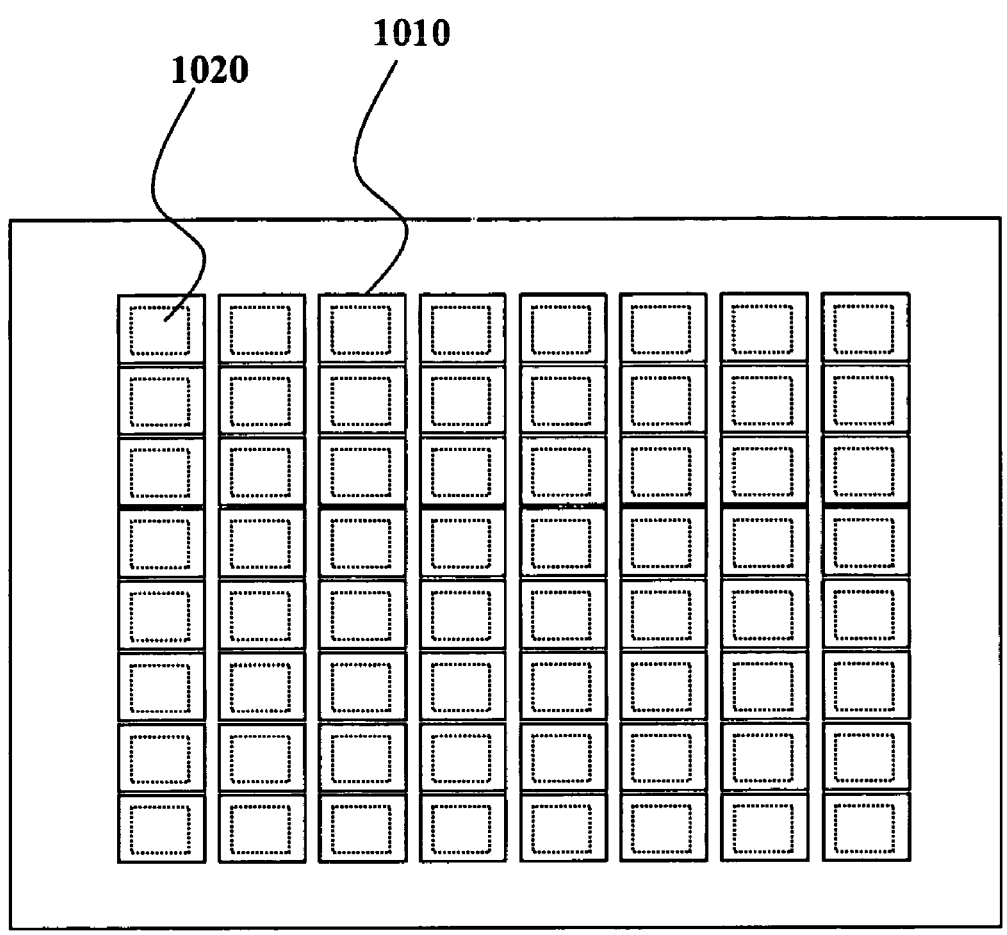
FIG. 10 shows a 64 well micro array prepared by wet etching silicon and adding sample wells.
Figure 11:
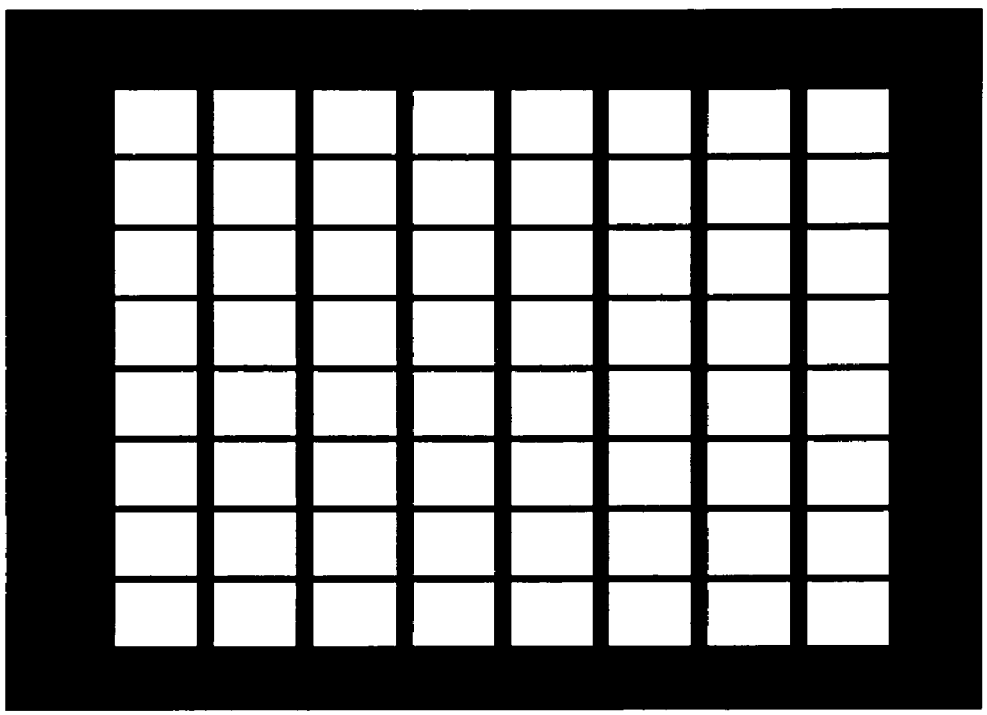
FIG. 11 shows an etch mask used for photolithography to make a 64 well micro array.
Figure 12:
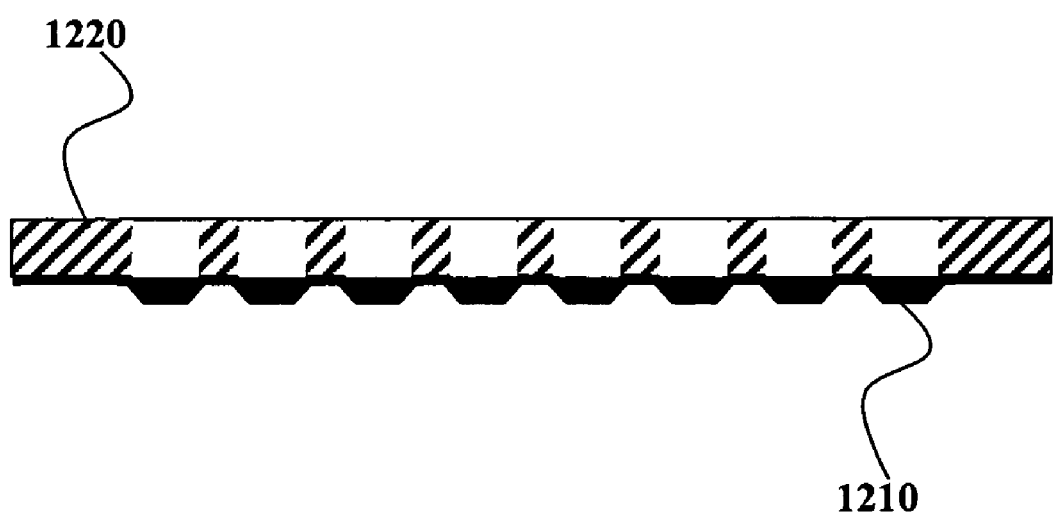
FIG. 12 is a cross sectional view of a 64 well micro array prepared by wet etching silicon.

As an illustration of this embodiment, a 64 well sample array shown in FIG. 10 is made by the following procedure. Standard photolithography is used to transfer the pattern for the etch mask shown in FIG. 11 to an oriented silicon substrate. Then, vapor deposition is used to create the etch mask. The etch mask is a thin film of a nitride but other materials such as an oxide may be used. Nitrides are preferred for the long etch period used to produce the deep grooves. In this example, the silicon pattern as shown in FIG. 11 etches at an angle of 54.7 degrees, creating prismatic grooves and pits. The silicon is etched with KOH although other anisotropic etchants may be used as well. At this point the lower prismatic surfaces are formed. The sample wells next are created in plastic and then wafer bonded to the top surface of the etched silicon component. The completed sample holder shown in the top view of FIG. 10 has 64 well openings 1010 with narrower bottoms 1020. The side view of FIG. 12 shows a lower section of silicon 1210 and an upper section of plastic sample wells 1220. Many materials, such as glass, or metal may be used for the sample wells. Optionally, vertical structures, such as the multiple internal reflection elements, can be created with either dry etching (reactive ion etching) or isotropic wet etching. In advantageous embodiments photolithography techniques are used to form larger arrays of at least 96 wells, 384 wells, 1024 wells, 5,000 wells, 10,000 wells, 25,000 wells, 50,000 wells, 100,000 wells, 250,000 wells, 500,000 wells and even more than 1,000,000 wells.

Internal elements are very useful for total internal reflection measurements and may be constructed by a variety of methods. One embodiment is a manufacturing process for making a large scale array of samples with total internal reflectance elements in them by binding one or more columns of polymer such as a plastic or protein to the inside surface(s) of each sample well. This embodiment is particularly useful for measurements using visible light. Many polymers do not absorb well between (for example) 400 and 800 nanometers and are useful for this embodiment. Total internal reflectance measurements may be carried out using a fluorescent probe and are particularly useful for this embodiment. The optical properties of the polymerized column may be corrected for and the system may be used in the near infrared, near ultraviolet, far infrared or far ultraviolet regions as well.

A polymer used to construct an internal reflectance element preferably is in the form of a rod between 0.5 microns and 100 microns wide, and more preferably between 1 and 10 microns wide. The rod preferably has a length at least twice, three times, five times and even more than ten times the width (mean measurements). The rod is at least partially transparent to the light being used and can be a natural product, a synthesized product, or even polymerized before or during the analysis. Many plastics are known but natural materials such as proteins may be used. Preferably, thermostable polypeptide(s) are used. Available materials include natural proteins such as elastin-, collagen-, keratin-, and silk-type proteins, preferably, proteins derived from thermophilic bacteria such as *Sulfolobus solfataricus* and *Thermus aquaticus* (enzymes such as proteases, DNA polymerases, lipases, and metabolic enzymes are especially useful), and more preferably, synthetic protein polymers, particularly proteins designed with silk-like protein, SLP blocks (SLPF or FCB-SLPIII (fibronectin), SLPL (laminin), SLPC (cystine), SLP3, SLP4, and SELPs (elastin) as described in U.S. patent application Ser. Nos. 609,716 and 114,618, and peptides designed with SLP blocks and other materials as described in U.S. Pat. No. 5,723,588 issued to Donofrio et al. The polypeptides may be natural, chemically synthesized, or recombinant proteins, including modified forms such as mutants and fusion products, and also including modifications against thermally induced degradation or denaturation, for example, pegylation. The proteins may be polymerized on the inside of the sample wells, or may be attached to those surfaces by covalent or non-covalent binding techniques.

In a particularly desirable embodiment samples in an sample array are manufactured having internal prismatic structures that are optically and/or physically coupled to a semiconductor foundation and have a dimension that extends away from that foundation of at least 10 microns long. Preferably the length (extending away from the surface is at least 1.5 time as long as the width, and more preferably at least 2 times, 3 times 5 times and even at least 10 times the width.

Super Broad Band System: Include Visible and Infrared Light In another embodiment of the invention, attenuated total internal reflectance spectroscopy is carried out on samples with both infrared and visible light. A single broadband beam that encompasses infrared and visible light may be used that is modulated by an interferometer. Alternatively a infrared light may be used as described herein and a separate visible light source beam additionally may be trained upon the sample holder. In the latter case, a common prismatic structure may be used for both infrared and visible light beams. The two beams may be directed into the prismatic structure at different angles to accommodate differential bending of light due to wavelengths.

In an embodiment, a spinning mirror interferometer, such as that used for infrared measurements is modified for an increased mirror rotational speed as necessary for the shorter wavelength light. Advances in light modulation technology in the future will provide more convenient alternative methods for generating suitable modulation and are contemplated for embodiments of the invention.

Fluorescence, phosphorescence, time resolved fluorescence and/or chemiluminescence may be used in conjunction with infrared techniques as described here. Drug discovery methods advantageously may utilize such added information to reveal further molecular and metabolic information. The additional information is helpful particularly for biochemical and cellular studies where the effects of a test compound in a sample are very complex and multiple chemical interactions need to be examined. For example, a cell may be genetically engineered to express luciferin and luciferase and generate light from a biochemical pathway and used as a probe in multiple sample wells to test for new lead drug compounds. Effects from the test compounds may be detected as visible light signals. By monitoring both infrared reflectance and visible light signals simultaneously, chemical binding of test compounds to a cell surface can be monitored, and the timing and effect on the biochemical process monitored. In one such embodiment a prismatic device may be used underneath a sample array for infrared reflectance measurements and an imaging visible light detector may be placed above the sample array to monitor the location and intensity of light obtained from the array. The detected visible light signals and the reflectance spectroscopy signals are processed and compared to generate information pertaining to each sample.

Timed addition In another embodiment a test substance or a chemical that controls a reaction may become available in the sample well from light activation. For example, a compound or set of compounds may be released by ultraviolet light acting upon a light sensitive labile chemical bond. Advantageously, a test compound is present, for example, on a wall of the sample container, and is released by a photoactivitable event. This embodiment is particularly useful for very large sample microassays of small size, wherein each individual sample well is very small (typically less than 10 microliters, less than 2, 1, 0.1 or even less than 0.01 microliters volume). The use of light activated chemistry in this embodiment alleviates the problem of having to administer test substances in very small volume at defined times. Light sensitive chemistries suitable for this embodiment are known. U.S. Pat. Nos. 5,798,491 and 5,714,328 issued to Magda et al. on Aug. 25, 1998 and Feb. 3, 1998 respectively, and a review by Keana and Cai in J. Org. Chem. 55: 3640–3647 (1990) provide representative examples. In practice a combinatorial library of molecules is generated and members of the library coupled via photo labile bonds to other molecule(s). The test molecules are liberated upon ultraviolet radiation.

An embodiment uses sample holders as described herein for a method of timed addition as follows. The surfaces of sample wells are divided into at least two surface coating types, a lower surface and one or more upper surfaces. The lower surface is within reach of a probing light used for total internal reflection. Preferably the lower surface in contact with the prismatic structure below extends upwards at least one wavelength distance of the probing light. The upper surface is too far away for significant optical interaction by a probing light evanescent wave. The upper surface(s) in an advantageous embodiment has attached to it a test substance or another activating substance that desirably is added to the sample solution at a defined time. That is, at the beginning of a test period, the test substance or other activator (compound or particle) is immobilized to an upper region of the wall and substantially out of reach of the probing light (which contacts the sample holder bottom). When a test is started, the immobilized substance(s) are released and their effects determined. The immobilized substances may be released by, for example, light catalyzed breakage of a link to the wall, sonication, change of air, electric discharge, or magnetic field. The released substances dissolve or become suspended in the sample fluid and can interact with components, such as cells and other molecules found there. The effects of the time released substances may be detected by total internal reflectance spectroscopy, using visible light, ultraviolet light or infrared light.

Definitions

To assist understanding of the embodiments and of the attached claims, the following definitions are provided.

The term "molecular interaction" means any interaction, including binding and catalytic interactions between at least two molecules. Binding interactions include for example binding between antibody binding site and antigen, binding between a protein and a ligand, such as between a membrane protein and an effector that binds the protein, and interactions determined indirectly by intracellular changes that occur upon addition of chemical substances that may act by binding to a cell membrane receptor, binding to effectors that bind to cell membrane receptors, thereby preventing effector binding to their receptors, and intracellular entry of a molecule that leads to some detectable change in another molecule or cellular process.

The term "wet samples" means samples that are in a fluid. The fluid may be an aqueous sample such as water, buffered saline, blood, interstitial fluid, sweat, urine and the like, but also may be non-aqueous such as xylene, dimethyl sulfoxide, dimethyl formamide, hexane, triglycerides, an alcohol and the like. Some binding reactions and some catalytic reactions have been studied using all organic (non aqueous) phase and such chemistries may be employed as well as aqueous chemistries. Gas phase reactions also may be included, where a binding molecule on the hydrated surface may bind to a volatile molecule. The concentration of and binding to an immobilized receptor or other binding substance on the surface of a material that experiences total internal reflection is included in the term "wet samples" as the surface of the well generally is hydrated.

The term "broadband infrared radiation" means multiple wavelengths suitable for determining a spectrum. Generally at least 3, more preferably at least 5 and even more preferably a large number of distinguishable wavelengths are included in the radiation. Preferably the bandwidth is at least 0.5 microns, more preferably at least 1 microns and even more preferably at least 2 or even at least 4 microns.

The term "optical interface" means having a defined solid structure that directs light such as probing light that enters one or more sample wells or positions, or modified light that leaves one or more sample wells or positions. An optical interface typically is an infrared transparent surface such as a prismatic portion of a larger surface or a separate optical structure that is positioned adjacent to or near another optical structure such as a sample holder or light source. The optical interface may for example effect the light passing through it to facilitate multiple internal reflectance in the optical interface or in another optical device. The optical interface effects light by virtue of one or more characteristics such as its refractive index, dimensions, and/or surface angle with respect to incident or exiting light.

The term "sample well" means a definable surface on or volume in an infrared radiation transparent material that holds a sample. A sample well may be a well of a 96 well microtiter plate wherein the bottom surface only is infrared radiation transparent. A sample well may be a three dimensional region corresponding to a position in an array that has been etched from a semiconductor chip surface. A sample well may be a surface having an immobilized substance. A flat surface without walls may nevertheless form an array of sample wells by virtue of chemical bonding that extends up from the surface immobilant. For example, a flat hydrophobic surface may be prepared by immobilizing a binding partner such as proteins, cells or other hydroscopic material in an array. Each binding partner is immobilized, for example as a hydroscopic dot upon a larger hydrophobic (water repelling) field. Contact of the surface with an aqueous solution will result in individual drops of water that adhere to the dots but not to the space between the dots. Each dot forms a well.

The term "optical contact" between a first part and a second part means that the two parts are positioned in direct contact or separated by a space such that light leaving one part (after reflection or passing through that part) and subsequently enters or reflects from the surface of the other part. In some cases optical contact is facilitated by physical contact between the surfaces of the two parts. An (refractive) index matching fluid, gel or soft material or paste may be interposed between the parts to fill any gaps between them and limit reflective loss. The index matching substance is transparent to the radiation used and has an index of refraction that is matched to the optical components.

The term "prismatic" means to bend light used in an optical measurement with respect to the surface of a target transparent medium such that the light enters the surface at an angle closer to the perpendicular of the target surface. A light transparent prism may be used in a prismatic fashion by choosing suitable angles and placement of the prism near to or in contact with the target.

The term "prismatically direct" with respect to a transparent optical structure means that the optical structure alters the path of light that passes through it by virtue of one or more controlled surface angles. As well appreciated by a skilled artisan, prisms are used to both split broadband light into different frequencies, combine broadband light into narrower bandwidths, and alter the direction of light passing through them.

The term "prismatic feature" means an optical feature whereby light passes through two surfaces of one or more optical structures in a manner that prismatically directs the light.

The term "internal reflection element" means a transparent optical structure such as a microstructure of an etched semiconductor chip, a protruding light pipe or channel into a sample well or a surface in contact with a sample that undergoes total internal reflection at the interface where contact with the sample occurs.

Other combinations of the inventive features described herein, of course can be easily determined by a skilled artisan after having read this specification, and are included in the spirit and scope of the claimed invention. The references cited above are specifically incorporated in their entireties by reference and represent art known to the skilled artisan.

We claim:
1. An instrument for simultaneous assay of molecular interaction in multiple samples via parallel vibration spectroscopy comprising:
   a) a source of broadband infrared radiation for probing molecular interactions with a modulator of broadband infrared radiation;
   b) a multiple-well sample holder comprising a substrate at least partially made of an infrared transparent material and etched to form an array of wells;
   c) a light directing optical structure having an optical interface with each sample well, wherein the optical structure directs modulated broadband infrared radiation to each said sample well allowing internal reflection and subsequent exit of the altered light;
   d) an infrared imaging radiation detector for simultaneously detecting the altered light; and
   e) a computer for analyzing data from the infrared imaging radiation detector.

2. The instrument of claim 1, wherein the light directing optical structure allows probing light to enter at near normal incidence, interact with multiple samples, and then exit.

3. The instrument of claim 2, wherein the infrared light director optic structure is prismatic or hemispheric.

4. The instrument of claim 1, wherein the light directing optical structure enables probing light to undergo multiple internal reflections at each sample well in the multiple well sample holder, wherein it interacts with each of the sample wells multiple times, and then exits.

5. The instrument of claim 4, wherein the light directing optical structure is prismatic.

6. The instrument of claim 4, wherein the light directing optical interfacing structure protrudes into each sample well of the multiple well sample holder.

7. The instrument of claim 6, wherein the light directing optical structure comprises a semiconductor substrate.

8. A multiple-well sample holder suitable for simultaneous assay of molecular interactions in multiple samples via parallel vibrational spectroscopy, comprising:
   a) a substrate at least partially made of an infrared transparent material having a sample surface and an optical interface, wherein;
   b) the sample surface of the infrared transparent substrate contains an array of multiple sample wells for accepting fluids, and
   c) the optical interface contains at least one light directing optical structure that directs broadband infrared radiation through the substrate, allowing internal reflection from the sample surface and the subsequent exit of the altered light; and
   d) the distance between the sample surface and the optical interface is greater than 1 micron.

9. The sample holder of claim 8, wherein
   a) the substrate is made of a semiconductor material;
   b) the array of multiple sample wells is etched in the substrate;
   c) the at least one light directing optical structure is a prism with a width of at least 20 microns and a height of at least 100 microns.

10. The sample holder of claim 8, wherein the at least one light directing optical structure protrudes into the sample volume.

11. The sample holder of claim 8, wherein the substrate and the light directing optical structure are formed from a single block of a semiconductor material by repeated etching.

12. A sample holder for the simultaneous assay of molecular interactions in multiple samples via parallel vibrational spectroscopy, comprising:
   a) an array of wells; and
   b) a prismatic structure contacting each sample well, wherein the prismatic structure comprises a material that is transparent to broadband infrared light of wavelengths between 5 and 10 microns, is at least twice as tall as it is wide and allows the light to enter the optically dense material with an incidence angle that exceeds the critical angle for total internal reflection.

13. The sample holder of claim 12, wherein the prismatic structure is in contact with a sample well bottom.

14. The sample holder of claim 13, wherein the prismatic structure has a portion protruding into the sample well through the sample bottom.

15. A tool for detecting effects of chemical compounds on cellular activities or for detecting desirable genetic manipulations in vitro, comprising:
   a) a source of broadband infrared radiation having wavelengths longer than 5 nanometers;
   b) a temperature controlled cell sample holder having an array of wells that hold and maintain metabolizing cells at a constant temperature in a wet environment, wherein each well has at least one surface in optical contact with the cells that is transparent to the infrared radiation;
   c) at least one prismatic structure having an optical interface with each sample well for directing the broadband infrared radiation into the infrared radiation transparent surfaces with an incidence angle that exceeds the critical angle for total internal reflection that penetrates a layer of cells in contact with the surface; and
   d) an infrared imaging detector that collects reflected light; and
   e) a computer for analyzing data from the infrared imaging radiation detector.

16. The tool of claim 15, wherein the cell sample holder has 96 wells and is dimensioned to be compatible with a microtiter plate.

17. The tool of claim 15, further comprising a computer controlled reagent addition apparatus for dispense of one or more reagents before or during collection of reflected light by the infrared imaging detector.

18. The tool of claim 15, wherein the infrared radiation has a wavelength longer than 10 nanometers.

19. The tool of claim 15, wherein the prismatic structure for each well protrudes into the well volume and provides multiple internal reflection.

20. The tool of claim 19, wherein the the prismatic structure contacts the well bottom.

21. The tool of claim 15, wherein the infrared imaging detector is arranged to collect spectra simultaneously from each sample, and the collected signal is processed by a Fourier transform processor.

22. A method for studying biomolecules in solution, comprising:
   a) providing a plurality of solution samples comprising biomolecules to be analyzed and at least one reference solution sample;
   b) inputting each one of the plurality of solution samples into an array of sample wells defined in a multiple well sample holder, wherein the array surface is transparent to broadband infrared radiation and is in optical contact with a prismatic structure that directs infrared light into the array surface with an incidence angle that exceeds the critical angle for total internal reflection that penetrates at least one tenth micron of the solution;

c) irradiating the array surface with broadband infrared radiation;

d) collecting reflected broadband light spectra from each well in the multiple well sample holder simultaneously using an imaging infrared detector;

e) comparing spectra from one or more sample wells to reference spectra from at least one reference sample well; and f) determining if there is any difference between the sample and the reference spectra.

23. The method of claim 22, wherein the step b) further comprises at least one biospecific capture step wherein at least one surface coupling ligand on the array surface binds to one or more molecules in solution and increases the concentration of the bound biomolecules within 2 microns of the surface prior to step c).

24. The method of claim 22, wherein comparing the sample spectra to the reference spectra includes binning the data from a plurality of pixels in the imaging detector.

25. The method of claim 22, wherein step b) further comprises at least one focusing step wherein the concentration of one or more molecules in solution is increased prior to step c).

26. A method for studying biomolecules in solution, comprising:
a) providing a plurality of solution samples comprising biomolecules to be analyzed, and relevant data from at least one reference sample;
b) inputting each one of the plurality of the samples into an array of sample wells defined in a multiple well sample holder, wherein the array surface is transparent to broadband infrared and is in optical contact with a prismatic structure that directs infrared light into the array surface with an incidence angle that exceeds the critical angle for total internal reflection that penetrates at least one tenth micron of the solution;

c) irradiating the array surface with broadband infrared radiation;

d) collecting the reflected broadband light spectra from each well in the multiple well sample holder simultaneously using an imaging infrared detector;

e) comparing the spectra from one or more sample wells to the data from at least one reference sample; and f) determining if there is any difference between the sample spectra and the reference data.

27. The method of claim 22, wherein step f) further comprises defining if the determined difference is due to the existence of binding interactions between molecules.

28. The method of claim 27, wherein step f) further comprises defining if the determined difference is due to the existence of binding interactions between molecules.

29. The method of claim 22, wherein step f) further comprises defining if the determined difference is due to the changes in the molecular structure of the biomolecules in the sample wells relative to the reference wells.

30. The method of claim 27, wherein step f) further comprises defining if the determined difference is due to the changes in the molecular structure of the biomolecules in the sample wells relative to the reference wells.

31. The method of claim 22, wherein step e) further comprises comparing the spectra from one or more sample wells to the data from at least one reference well at multiple points in time to determine reaction kinetics.

32. The method of claim 27, wherein step e) further comprises comparing the spectra from one or more sample wells to the data from at least one reference sample at multiple points in time to determine reaction kinetics.

* * * * *